(12) United States Patent
Bartish, Jr. et al.

(10) Patent No.: US 7,690,381 B2
(45) Date of Patent: Apr. 6, 2010

(54) INTERVERTEBRAL PROSTHETIC DISC AND METHOD FOR INSTALLING USING A GUIDEWIRE

(75) Inventors: Charles M. Bartish, Jr., Providence, RI (US); Katherine Torres, North Dartmouth, MA (US); J. Riley Hawkins, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 142 days.

(21) Appl. No.: 11/055,566

(22) Filed: Feb. 10, 2005

(65) Prior Publication Data

US 2006/0178746 A1 Aug. 10, 2006

(51) Int. Cl.
*A61F 2/44* (2006.01)
(52) U.S. Cl. ..................................................... 128/898
(58) Field of Classification Search ... 623/17.11–17.16, 623/113; 606/61, 79, 99
See application file for complete search history.

(56) References Cited

U.S. PATENT DOCUMENTS

| | | | |
|---|---|---|---|
| 3,867,728 A | | 2/1975 | Stubstad, et al. |
| 3,875,595 A | * | 4/1975 | Froning .................... 623/17.12 |
| 4,349,921 A | * | 9/1982 | Kuntz ....................... 623/17.16 |
| 4,759,769 A | * | 7/1988 | Hedman et al. .......... 623/17.13 |
| 4,772,287 A | | 9/1988 | Ray et al. |
| 4,904,260 A | | 2/1990 | Ray et al. |
| 5,192,327 A | * | 3/1993 | Brantigan ................. 623/17.11 |
| 5,395,317 A | * | 3/1995 | Kambin ....................... 604/506 |
| 5,397,364 A | * | 3/1995 | Kozak et al. ............. 623/17.11 |
| 5,425,772 A | * | 6/1995 | Brantigan ................. 623/17.11 |
| 5,425,773 A | | 6/1995 | Boyd et al. |
| 5,458,638 A | * | 10/1995 | Kuslich et al. ........... 623/17.11 |
| 5,458,642 A | * | 10/1995 | Beer et al. ................ 623/17.13 |
| 5,545,168 A | * | 8/1996 | Burke .......................... 606/74 |
| 5,549,679 A | * | 8/1996 | Kuslich .................... 623/17.12 |
| 5,658,335 A | * | 8/1997 | Allen ....................... 623/17.16 |
| 5,702,450 A | * | 12/1997 | Bisserie ................... 623/17.16 |
| 5,716,416 A | * | 2/1998 | Lin ........................... 623/17.16 |
| 5,861,041 A | * | 1/1999 | Tienboon ................. 623/17.16 |
| 5,928,284 A | | 7/1999 | Mehdizadeh |
| 6,019,792 A | | 2/2000 | Cauthen |
| 6,110,210 A | * | 8/2000 | Norton et al. ............ 623/17.16 |
| 6,149,686 A | * | 11/2000 | Kuslich et al. ........... 623/17.11 |
| 6,159,211 A | * | 12/2000 | Boriani et al. ............... 606/61 |
| 6,179,874 B1 | | 1/2001 | Cauthen |
| 6,206,922 B1 | * | 3/2001 | Zdeblick et al. ......... 623/17.11 |
| 6,231,609 B1 | | 5/2001 | Mehdizadeh |
| 6,241,769 B1 | * | 6/2001 | Nicholson et al. ....... 623/17.11 |

(Continued)

FOREIGN PATENT DOCUMENTS

DE 197 20 241 A1 11/1998

(Continued)

*Primary Examiner*—David J Isabella
*Assistant Examiner*—Ann Schillinger

(57) ABSTRACT

The present invention includes an intervertebral prosthetic disc, a method for installing a plate into an intervertebral space, and a method for installing a prosthetic disc into an intervertebral space. The intervertebral prosthetic disc can include a superior endplate and an inferior endplate, wherein at least one of the superior endplate and the inferior endplate is adapted to receive a guidewire. In the methods for installing a plate into an intervertebral space and for installing a prosthetic disc into an intervertebral space, a guidewire is used to facilitate installing plates onto vertebral bone endplates.

27 Claims, 12 Drawing Sheets

U.S. PATENT DOCUMENTS

| | | | |
|---|---|---|---|
| 6,245,108 B1* | 6/2001 | Biscup | 623/17.11 |
| 6,368,351 B1 | 4/2002 | Glenn et al. | |
| 6,419,704 B1* | 7/2002 | Ferree | 623/17.12 |
| 6,436,139 B1* | 8/2002 | Shapiro et al. | 623/17.11 |
| 6,440,168 B1 | 8/2002 | Cauthen | |
| 6,454,806 B1* | 9/2002 | Cohen et al. | 623/17.15 |
| 6,454,807 B1* | 9/2002 | Jackson | 623/17.15 |
| 6,554,863 B2* | 4/2003 | Paul et al. | 623/17.11 |
| 6,558,390 B2* | 5/2003 | Cragg | 606/80 |
| 6,572,653 B1* | 6/2003 | Simonson | 623/17.13 |
| 6,575,979 B1* | 6/2003 | Cragg | 606/86 |
| 6,579,321 B1 | 6/2003 | Gordon et al. | |
| 6,592,624 B1* | 7/2003 | Fraser et al. | 623/17.16 |
| 6,599,294 B2* | 7/2003 | Fuss et al. | 606/99 |
| 6,610,093 B1 | 8/2003 | Pisharodi | |
| 6,613,091 B1* | 9/2003 | Zdeblick et al. | 623/17.16 |
| 6,648,917 B2* | 11/2003 | Gerbec et al. | 623/17.11 |
| 6,679,915 B1 | 1/2004 | Cauthen | |
| 6,692,495 B1 | 2/2004 | Zacouto | |
| 6,706,067 B2* | 3/2004 | Shimp et al. | 623/17.11 |
| 6,749,635 B1 | 6/2004 | Bryan | |
| 6,800,092 B1 | 10/2004 | Williams et al. | |
| 6,835,206 B2* | 12/2004 | Jackson | 623/17.11 |
| 7,153,325 B2* | 12/2006 | Kim et al. | 623/17.15 |
| 2002/0032483 A1* | 3/2002 | Nicholson et al. | 623/17.11 |
| 2002/0049497 A1* | 4/2002 | Mason | 623/17.11 |
| 2002/0082600 A1* | 6/2002 | Shaolian et al. | 606/61 |
| 2002/0099444 A1* | 7/2002 | Boyd et al. | 623/17.16 |
| 2002/0161443 A1* | 10/2002 | Michelson | 623/17.11 |
| 2002/0183848 A1* | 12/2002 | Ray et al. | 623/17.12 |
| 2003/0040802 A1 | 2/2003 | Errico et al. | |
| 2003/0060889 A1* | 3/2003 | Tarabishy | 623/22.12 |
| 2003/0069586 A1* | 4/2003 | Errico et al. | 606/99 |
| 2003/0069639 A1* | 4/2003 | Sander et al. | 623/17.11 |
| 2003/0069643 A1* | 4/2003 | Ralph et al. | 623/17.13 |
| 2003/0120344 A1* | 6/2003 | Michelson | 623/17.11 |
| 2003/0125739 A1* | 7/2003 | Bagga et al. | 606/61 |
| 2003/0199982 A1 | 10/2003 | Bryan | |
| 2003/0204261 A1* | 10/2003 | Eisermann et al. | 623/17.14 |
| 2004/0002759 A1* | 1/2004 | Ferree | 623/17.11 |
| 2004/0010316 A1* | 1/2004 | William et al. | 623/17.16 |
| 2004/0024461 A1* | 2/2004 | Ferree | 623/17.13 |
| 2004/0024462 A1* | 2/2004 | Ferree et al. | 623/17.14 |
| 2004/0030387 A1* | 2/2004 | Landry et al. | 623/16.11 |
| 2004/0034426 A1* | 2/2004 | Errico et al. | 623/17.13 |
| 2004/0044410 A1 | 3/2004 | Ferree et al. | |
| 2004/0049280 A1 | 3/2004 | Cauthen | |
| 2004/0102846 A1* | 5/2004 | Keller et al. | 623/17.11 |
| 2004/0111155 A1* | 6/2004 | Ferree | 623/17.13 |
| 2004/0127991 A1 | 7/2004 | Ferree | |
| 2004/0138749 A1 | 7/2004 | Zucherman et al. | |
| 2004/0138753 A1* | 7/2004 | Ferree | 623/17.11 |
| 2004/0143270 A1 | 7/2004 | Zucherman et al. | |
| 2004/0153159 A1 | 8/2004 | Cauthen | |
| 2004/0158254 A1 | 8/2004 | Eisermann | |
| 2004/0158328 A1* | 8/2004 | Eisermann | 623/17.16 |
| 2004/0181284 A1 | 9/2004 | Simonson | |
| 2004/0181285 A1 | 9/2004 | Simonson | |
| 2004/0186471 A1* | 9/2004 | Trieu | 606/61 |
| 2004/0186572 A1* | 9/2004 | Lange et al. | 623/17.11 |
| 2004/0186577 A1 | 9/2004 | Ferree | |
| 2004/0193271 A1* | 9/2004 | Fraser et al. | 623/17.11 |
| 2004/0193273 A1* | 9/2004 | Huang | 623/17.12 |
| 2004/0215342 A1* | 10/2004 | Suddaby | 623/17.12 |
| 2004/0225362 A1* | 11/2004 | Richelsoph | 623/17.13 |
| 2004/0225365 A1 | 11/2004 | Eisermann et al. | |
| 2004/0225366 A1 | 11/2004 | Eisermann et al. | |
| 2004/0236425 A1* | 11/2004 | Huang | 623/17.12 |
| 2004/0243238 A1* | 12/2004 | Arnin et al. | 623/17.12 |
| 2004/0254644 A1* | 12/2004 | Taylor | 623/17.13 |
| 2005/0027364 A1 | 2/2005 | Kim et al. | |
| 2005/0055098 A1* | 3/2005 | Zdeblick et al. | 623/17.11 |
| 2005/0113916 A1* | 5/2005 | Branch | 623/17.11 |
| 2005/0154459 A1* | 7/2005 | Wolek et al. | 623/17.11 |
| 2005/0187625 A1* | 8/2005 | Wolek et al. | 623/17.11 |
| 2005/0216084 A1* | 9/2005 | Fleischmann et al. | 623/17.11 |
| 2005/0240267 A1* | 10/2005 | Randall et al. | 623/17.11 |

FOREIGN PATENT DOCUMENTS

| | | |
|---|---|---|
| EP | 1 374 808 A | 1/2004 |
| WO | WO 2004/098466 A2 | 11/2004 |

* cited by examiner

INTERVERTEBRAL PROSTHETIC DISC AND METHOD FOR INSTALLING USING A GUIDEWIRE

BACKGROUND OF THE INVENTION

The human spinal column consists of discrete, sequentially coupled bones, i.e., vertebrae, cushioned by cartilaginous spacers, i.e., intervertebral discs, disposed between opposing vertebral bone endplates. Intervertebral discs are generally elastic, allowing the spine to retain a high degree of flexibility. When a disc, or a portion of a disc, wears out or is injured, the disc cannot function normally and the failed disc can cause pain to a patient or limit the patient's activities. Therefore, surgery is often recommended when an intervertebral disc fails, for example, due to disease, infection, deformity, or fracture. Surgery can sometimes help to reduce attendant pain and restore at least some level of activity to the patient. Surgery can include implantation of an artificial disc or other prosthetic devices that restore the height of the spinal column and a natural angle between the adjacent vertebrae. For example, surgery can include spinal fusion or disc replacement. Spinal fusion can be effective in reducing pain, but it limits the range of motion of the spine and it can result in transfer of extra stress to discs above and below the fusion site. Generally, known artificial discs offer several benefits over spinal fusion, including pain reduction and a potential to avoid premature degeneration at adjacent levels of the spine by maintaining normal spinal motion.

Commonly, implantation of an artificial disc is performed using an anterior approach. For example, two surgeons typically work together in performing an anterior approach artificial disc implantation. A general or vascular surgeon approaches the spine through an incision in the abdomen and carefully moves internal organs and blood vessels to provide access to the spine. A spine surgeon then removes the damaged disc, prepares the intervertebral space for implantation of the artificial disc, and inserts the artificial disc into the intervertebral space. Post-operative complications can include abdominal wall hematoma, vascular injury, retrograde ejaculation, and gastrointestinal injury following implantation of an artificial disc.

A need exists for an intervertebral prosthetic device and a method for placing an intervertebral prosthetic device that overcomes or minimizes the above-referenced problems.

SUMMARY OF THE INVENTION

The present invention includes an intervertebral prosthetic disc, a method for installing a plate into an intervertebral space, and a method for installing a prosthetic disc into an intervertebral space. The intervertebral prosthetic disc can include a superior endplate and an inferior endplate, wherein at least one of the superior endplate and the inferior endplate is adapted to receive a guidewire. In the methods for installing a plate into an intervertebral space and for installing a prosthetic disc into an intervertebral space, a guidewire is used to facilitate installing plates onto vertebral bone endplates.

In one embodiment, the intervertebral prosthetic disc includes a superior endplate and an inferior endplate, wherein at least one of the superior endplate and the inferior endplate is adapted to receive a guidewire. The intervertebral prosthetic disc also can include a core positioned between the superior endplate and the inferior endplate. In another embodiment, the superior endplate and the inferior endplate include a ball component and a socket component for receiving the ball component. In one embodiment, at least one of the superior endplate and the inferior endplate defines a guidewire channel with a generally lateral-medial orientation.

The present invention also includes a method for installing a plate into an intervertebral space. The method can include threading a first plate onto a first guidewire, wherein the first plate is adapted to receive the first guidewire; inserting the first plate into the intervertebral space; tensioning the first guidewire; and seating the first plate onto a first vertebral bone endplate. In one embodiment, the method further includes threading a second plate onto a second guidewire, wherein the second plate is adapted to receive the second guidewire; inserting the second plate into the intervertebral space; tensioning the second guidewire; and seating the second plate onto a second vertebral bone endplate. Preferably, a posterior or posterior-lateral surgical approach can be used to install the plate(s) into the intervertebral space.

In one aspect of the invention, a method for installing a prosthetic disc which includes a first plate, a second plate, and a core into an intervertebral space is provided herein. The method includes threading the first plate onto a first guidewire, wherein the first plate is adapted to receive the first guidewire; threading the second plate onto a second guidewire, wherein the second plate is adapted to receive the second guidewire; inserting the first plate and the second plate into the intervertebral space; tensioning the first and second guidewires; seating the first plate onto a superior vertebral bone endplate and seating the second plate onto an inferior vertebral bone endplate; and positioning the core between the first plate and the second plate. Preferably, a posterior or posterior-lateral surgical approach can be used to install the prosthetic disc into the intervertebral space.

In addition, a method for installing a prosthetic disc which includes a first plate and a second plate into an intervertebral space is provided herein. This method includes threading the first plate onto a first guidewire, wherein the first plate is adapted to receive the first guidewire; threading the second plate onto a second guidewire, wherein the second plate is adapted to receive the second guidewire; inserting the first plate and the second plate into the intervertebral space; tensioning the first and second guidewires; and positioning the first plate and the second plate within the intervertebral space.

By practicing the present invention, an intervertebral prosthetic disc can be inserted using a posterior or a posterior-lateral approach. A posterior or a posterior-lateral procedure to intervertebral disc replacement is typically less invasive than an anterior procedure. Complications related to anterior procedures can be reduced or eliminated by practicing the present invention. In some embodiments, the services of a vascular surgeon needed to access the intervertebral disc space are reduced or eliminated.

By practicing the present invention, a surgeon can obtain precise location of the prosthetic disc's endplates relative to the vertebral bodies. The present invention can provide the surgeon with the ability to finely adjust the location of the intervertebral disc to ensure proper disc function. By practicing the invention, pieces of an endplate can be connected with relative ease within the intervertebral space. As a result, smaller devices can be inserted through smaller exposures and assembled in vivo.

The intervertebral prosthetic discs of the present invention can have a generally larger surface area for contact with the vertebral bone endplates than would be expected in a device inserted using a posterior or posterior-lateral approach. A generally larger surface area for contact with the vertebral bone endplates can reduce or eliminate subsidence of the intervertebral prosthetic disc.

The intervertebral prosthetic discs of the present invention can provide for translation motion as well as rotation motion when surgically installed in the spinal column. Practice of the present invention can also expand the patient population that can benefit from installation of an intervertebral prosthetic disc by providing a method and disc for posterior insertion into an intervertebral space. For example, in one embodiment, the present invention can be practiced for patients having posterior-lateral herniations.

DETAILED DESCRIPTION OF THE INVENTION

Figure 1A:
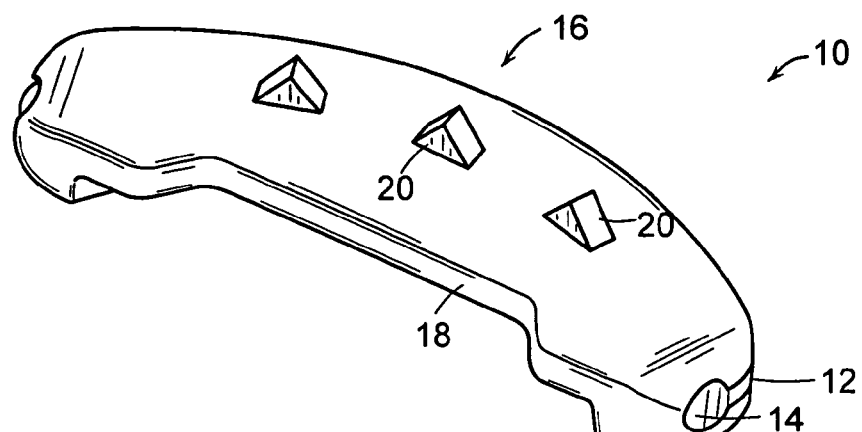
FIG. 1A is a perspective view of one embodiment of the present invention wherein an anterior plate of an endplate is adapted to receive a guidewire.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention includes an intervertebral prosthetic disc. In one embodiment, the prosthetic disc includes a superior endplate and an inferior endplate, wherein at least one of the superior endplate and the inferior endplate is adapted to receive a guidewire. For example, at least one of the superior endplate and the inferior endplate can define a guidewire channel. In one particular embodiment, the guidewire channel has a generally a lateral-medial orientation within an endplate. The endplates can have an anterior edge and a posterior edge, defined with reference to the endplate as positioned in an intervertebral space. In one embodiment, the anterior edge of the endplate is curved. In one embodiment, the guidewire channel lies along the anterior edge of the endplate and has a generally a lateral-medial orientation within the endplate that follows the curvature of the anterior edge. The endplate can also define a space integral with the guidewire channel for receiving a guidewire stop.

The guidewire can be constructed of any material capable of sterilization and having a tensile strength appropriate for tensioning as described infra. In one embodiment, the guidewire is a stainless steel wire or cable. Alternatively, the guidewire is a titanium or nitinol wire or cable. The guidewire have a variety of sizes and diameters depending on the size of the guidewire channel. In one embodiment, the guidewire has a diameter of about 0.75 to about 1.2 millimeters. In a preferred embodiment, the guidewire includes a guidewire stop that abuts the endplate upon threading the endplate with the guidewire. The guidewire stop can be, for example, a ball (e.g., a metal ball) or a knot.

In one embodiment, at least one of the superior endplate and the inferior endplate includes a protrusion element. Protrusion elements can be used to increase the surface area of an endplate that is presented to a vertebral bone endplate. Protrusion elements are further described in U.S. patent application Ser. No. 11/055,025, entitled "Intervertebral Prosthetic Disc," filed on even date herewith, the entire contents of which are incorporated herein by reference. In one embodiment, at least one of the superior endplate and the inferior endplate is adapted to receive the protrusion element. At least one of the superior endplate and the inferior endplate can include a plurality of protrusion elements.

One or both of the superior endplate and the inferior endplate can include vertebral bone endplate anchor elements. The anchor elements are generally capable of penetrating a vertebral bone endplate. Examples of anchor elements can include, but are not limited to, keels, spikes, teeth, fins, and pegs. In some embodiments, one or both of the superior endplate and the inferior endplate can include a textured surface that facilitates bone growth. For example, the textured surface can include at least one member selected from the group consisting of porous beading, hydroxyapatite, and mesh. In one embodiment, one or both of the superior endplate and the inferior endplate can include an osteoinductive material. Osteoinductive materials suitable for use include, for example, titanium, cobalt-chromium, nitinol, stainless steel, polyethylene, polyester, polyurethane, silicone, polycarbonate, zirconia, alumina, hydroxyapatite, tricalcium phosphate, collagen, bone morphogenic proteins, demineralized bone matrices, and growth factors.

In one aspect of the invention, at least one endplate can include an anterior plate and a posterior plate. The superior endplate can include a first anterior plate and a first posterior plate. The inferior endplate can include a second anterior plate and a second posterior plate.

Figure 1B:
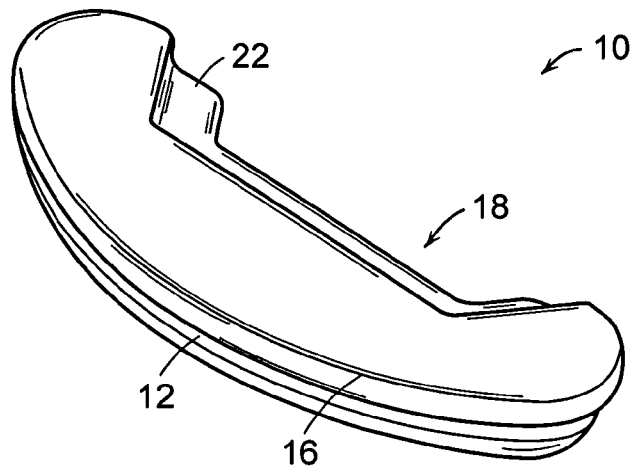
FIG. 1B is another perspective view of the anterior plate of FIG. 1A.

FIGS. 1A-1B illustrate an anterior plate according to one embodiment of the present invention. Anterior plate 10 defines guidewire channel 12 and contains guidewire stop space 14. Guidewire channel 12 can lie along anterior edge 16 of anterior plate 10. Anterior plate 10 also includes posterior edge 18. Anterior plate 10 can include vertebral bone endplate anchor elements 20. Anchor elements 20 are generally capable of penetrating a vertebral bone endplate. Examples of anchor elements 20 can include, but are not limited to, keels, spikes, teeth, fins, and pegs. The anterior plate can be adapted for affixation to a posterior plate, described infra. For example, anterior plate 10 can define interface 22, e.g., a cantilever or ledge, for joining anterior plate 10 with the posterior plate, thereby forming an endplate. In one embodiment not illustrated, interface 22 is a dovetail interface.

Figure 2A:
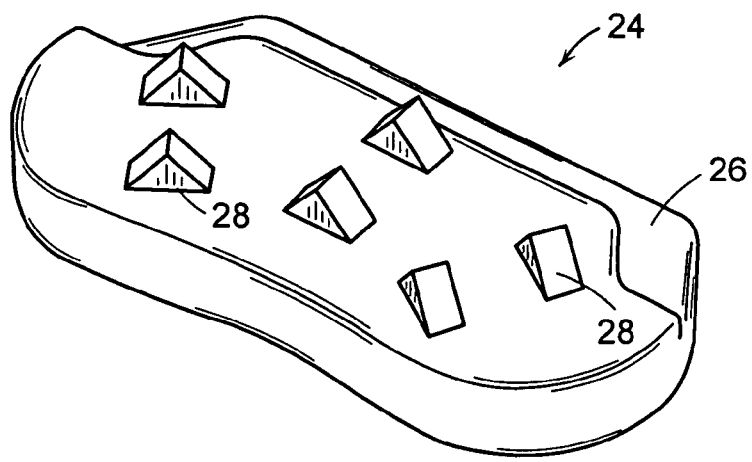
FIG. 2A is a perspective view of a posterior plate of an endplate according to one embodiment of the present invention.

FIG. 2A illustrates a posterior plate according to one embodiment of the present invention. Posterior plate 24 can define interface 26, e.g., a cantilever, ledge or dovetail, for joining posterior plate 24 with an anterior plate, e.g., anterior plate 10, thereby forming an endplate. Posterior plate 24 can also include vertebral bone endplate anchor elements 28. Anchor elements 28 are generally capable of penetrating a vertebral bone endplate. Examples of anchor elements 28 can include, but are not limited to, keels, spikes, teeth, fins, and pegs. While not illustrated, posterior plate 24 can define a guidewire channel. In one embodiment, posterior plate 24 defines a guidewire channel and anterior plate 10 does not define a guidewire channel.

Figure 2B:
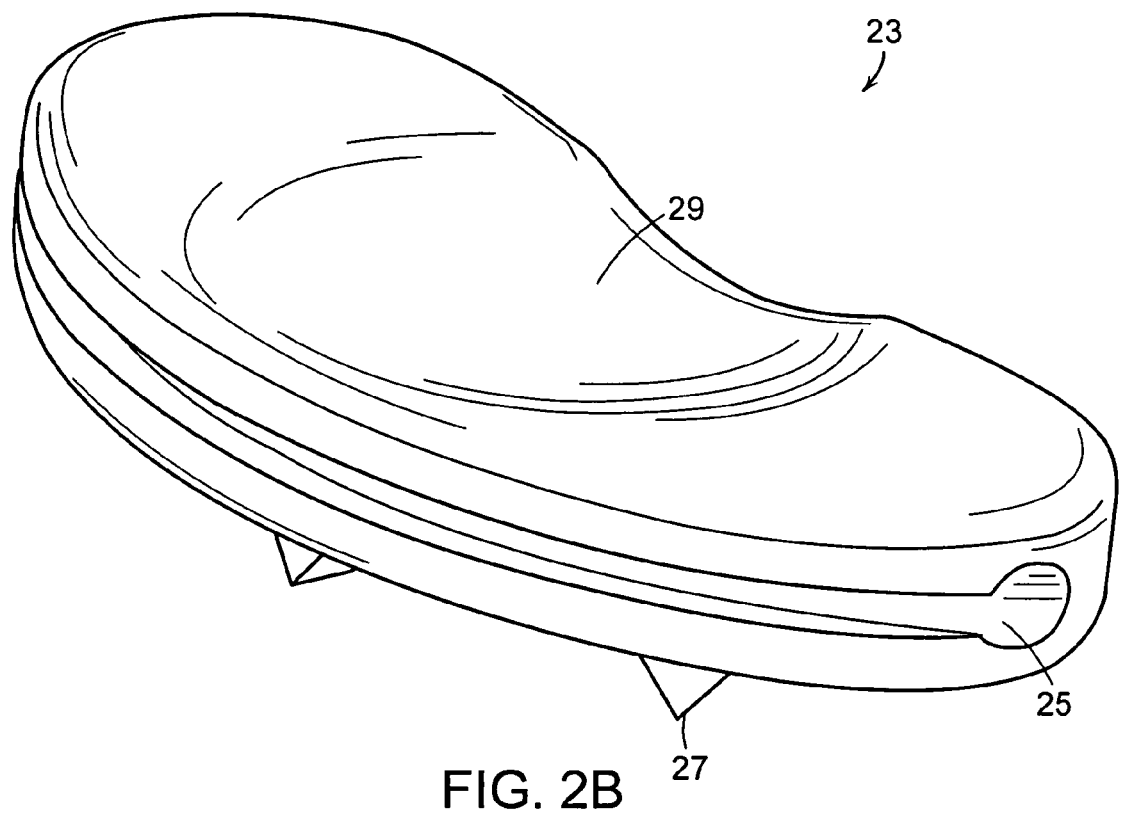
FIGS. 2B and 2C are perspective views of endplate embodiments.
Figure 2C:
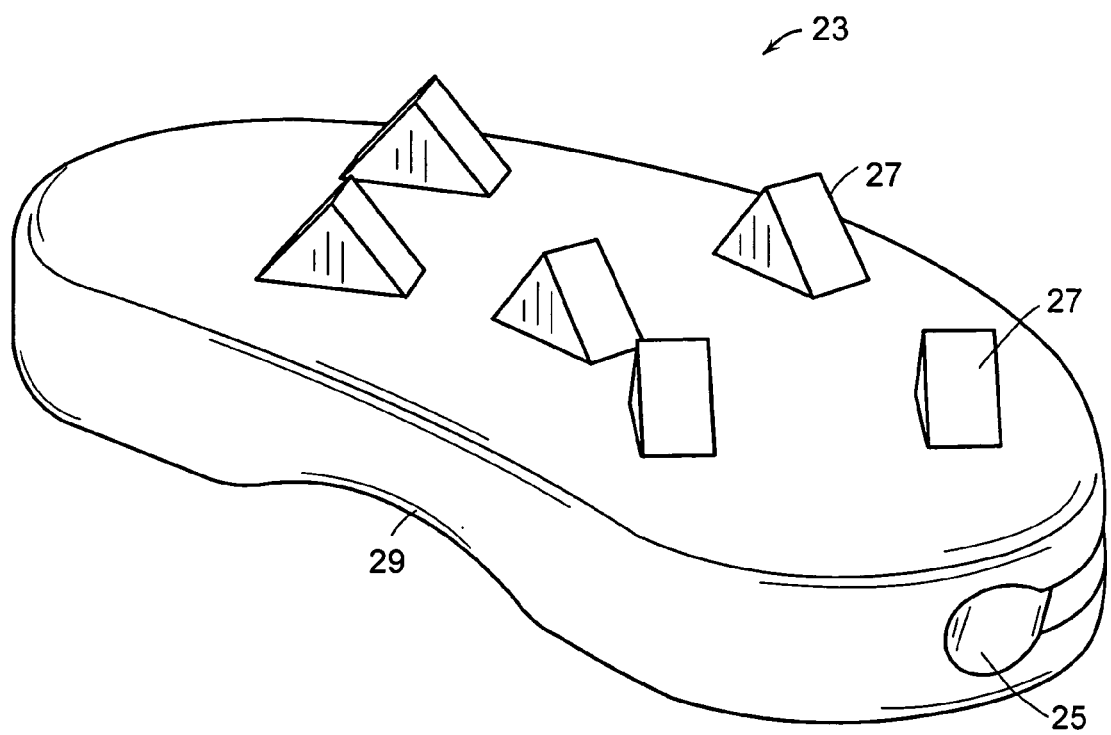

FIGS. 2B and 2C illustrate endplate 23 according to one embodiment of the present invention. Endplate 23 can also include vertebral bone endplate anchor elements 27. Anchor elements 27 are generally capable of penetrating a vertebral bone endplate. Examples of anchor elements 27 can include, but are not limited to, keels, spikes, teeth, fins, and pegs. Endplate can include recess 29 for receiving a core or a ball component. In one embodiment, endplate 23 defines guidewire channel 25.

Figure 2D:
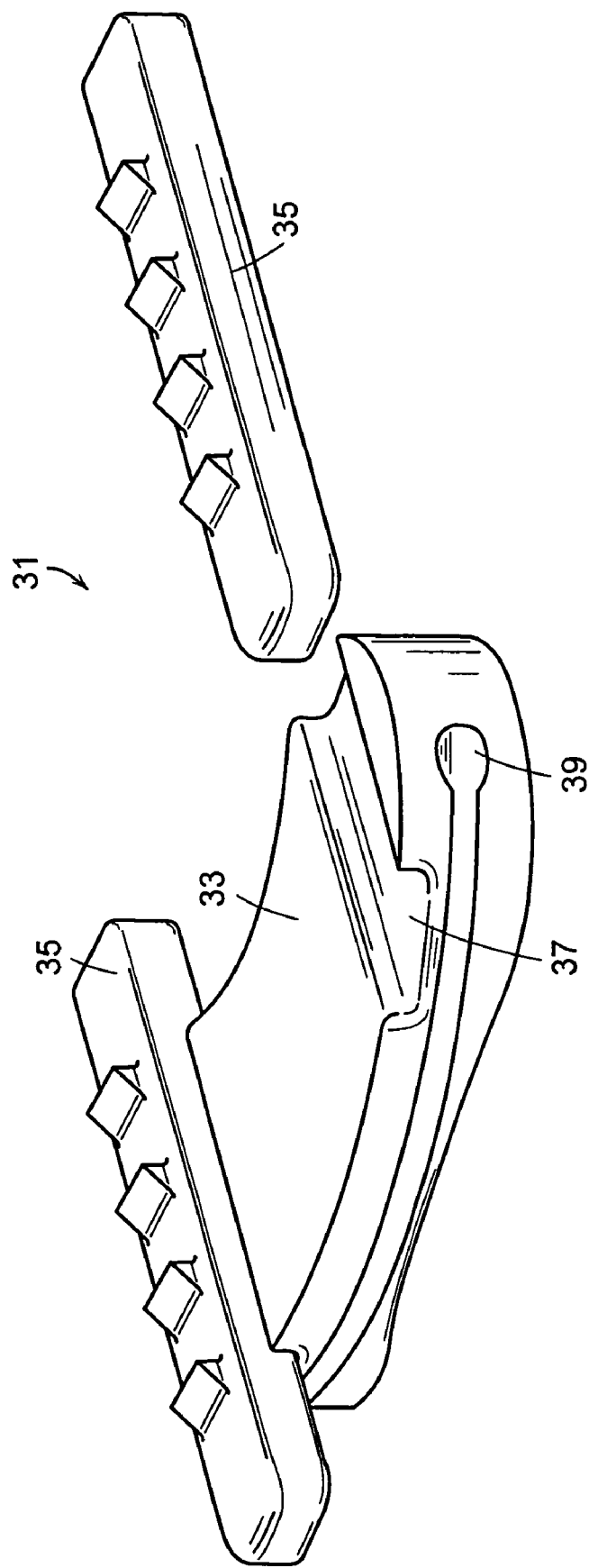
FIG. 2D is a perspective view of an example of assembly of an intervertebral prosthetic disc endplate that includes protrusion elements and a guidewire channel.

FIG. 2D illustrates endplate assembly 31 according to one embodiment of the present invention. Endplate assembly 31 includes endplate 33 and protrusion elements 35. As illustrated, protrusion element 35 is joined to endplate 33 through groove 37 defined by the endplate. For example, protrusion element 35 is fitted into groove 37. Endplate assembly 31 also includes guidewire channel 39.

Figure 3:
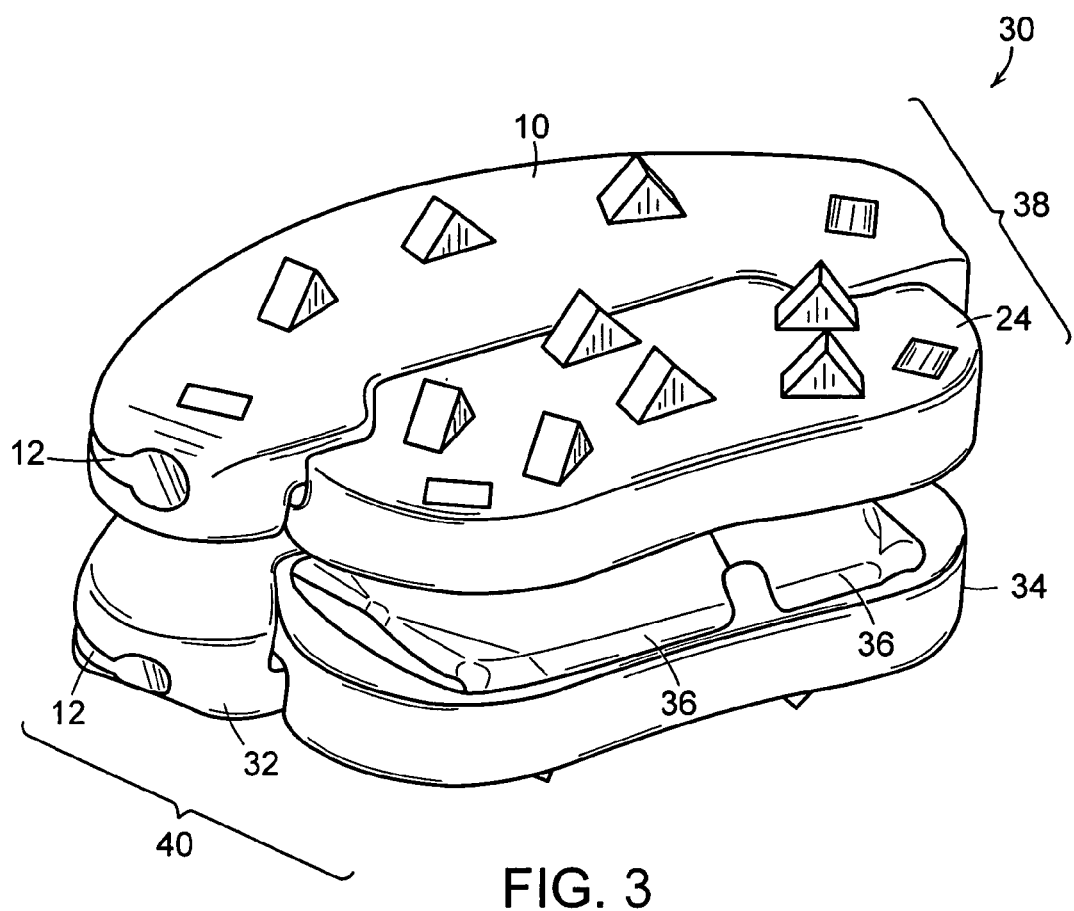
FIG. 3 is a perspective view of an intervertebral prosthetic disc according to one embodiment of the present invention.

FIG. 3 shows an example of assembled intervertebral prosthetic disc 30. Intervertebral prosthetic disc 30 includes first endplate 38 that includes anterior plate 10 and posterior plate 24 and second endplate 40 that includes anterior plate 32 and posterior plate 34. Anterior plate 32 and posterior plate 34 can be substantially similar to anterior plate 10 and posterior plate 24, but can differ in the number and configuration of recesses that are defined therein, described infra. Core module 36 can be accommodated by recesses defined in endplates 38 and 40. For example, as illustrated in FIG. 3, core module 36 can be accommodated by recesses defined in posterior plates 24 and 34.

In one embodiment, anterior plate 10 and posterior plate 24 interlock to form endplate 38. Anterior plate 32 and posterior plate 34 can interlock to form endplate 40. Anterior and posterior plates 10 and 24 and anterior and posterior plates 32 and 34 can also, or alternatively, be fixed together with a fastener such as, for example, a peg or a screw. In one embodiment, an anterior plate and a posterior plate are joined together within the intervertebral space to form an endplate.

One or both of anterior and posterior plates 10 and 24 can be adapted to receive a guidewire. For example, in one embodiment, anterior plate 10 defines a guidewire channel. Likewise, one or both of anterior and posterior plates 32 and 34 can be adapted to receive a guidewire. For example, in one embodiment, anterior plate 32 defines a guidewire channel.

As illustrated in FIG. 3, in one embodiment, both endplates 38 and 40 each include an anterior plate and a posterior plate. The endplates 38 and 40 and any components thereof can be constructed of any of the materials known in the art for use in a prosthetic disc. For example, the endplates and any components thereof can be constructed of medical grade cobalt chromium alloy.

As illustrated in FIG. 3, intervertebral prosthetic disc 30 also has a core, which include core modules 36, positioned between endplates 38 and 40. The core is typically separated from the vertebral bone endplates by endplates 38 and 40. In one embodiment, the core is resilient. The core can be constructed of any of the materials known in the art for use in a prosthetic disc core. In a preferred embodiment, the core is constructed of a medical grade plastic with good sliding properties with respect to the endplate materials. In one embodiment, the core is polyethylene, for example, high density polyethylene.

In one embodiment not illustrated, the core is a one-component core. Alternatively, the core can include a plurality of core modules 36. Core modules 36 are constructed of the materials described supra. In one embodiment, the core includes two core modules 36. In one aspect of the invention, core modules 36 mate or abut, thereby constraining movement relative to one another, e.g., lateral-medial movement can be constrained. For example, in one embodiment, core modules 36 are adapted to mate or abut so as to constrain lateral-medial movement relative to one another.

Figure 4:
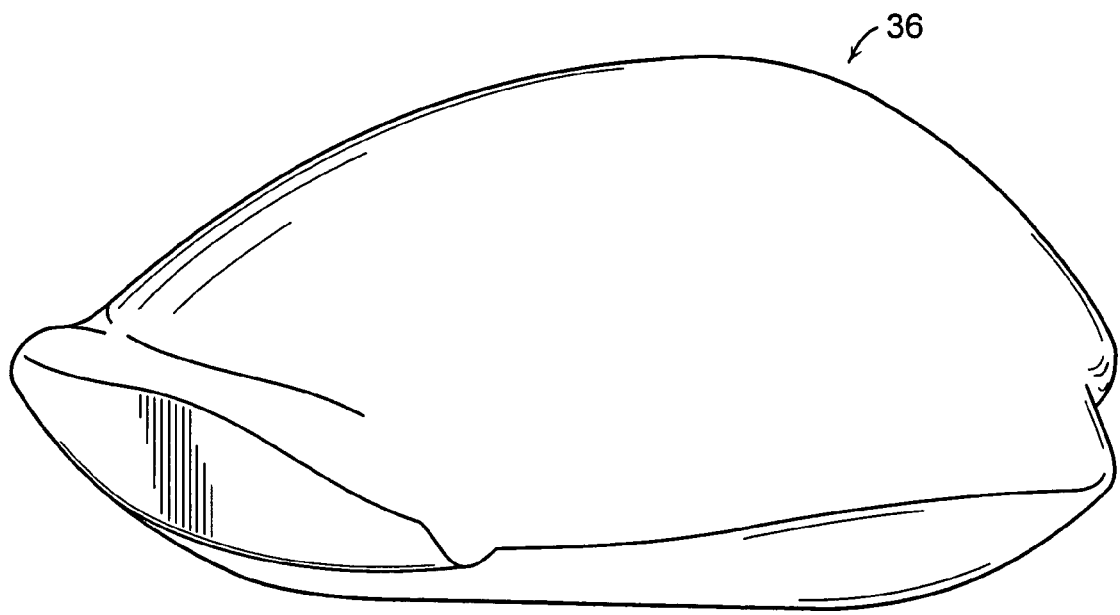
FIG. 4 is a view of an example of a core module.

FIG. 4 illustrates example core module 36.

Figure 5:
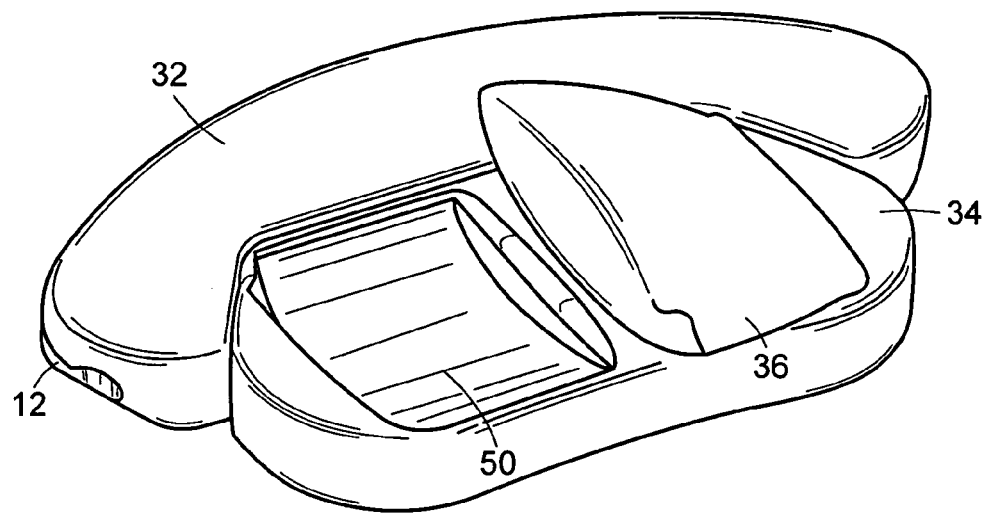
FIG. 5 is a perspective view of a partially assembled intervertebral prosthetic disc according to one embodiment of the present invention.

FIG. 5 shows a partially assembled intervertebral prosthetic disc illustrated in FIG. 3. Posterior plate 34 is illustrated having truncated cylindrical recess 50 wherein core module 36 can be accommodated. In one embodiment, recess 50 constrains the core from substantial lateral-medial movement relative to the superior endplate and the inferior endplate. Recess 50 can assume a variety of geometries. For example, recess 50 can be a truncated cylindrical recess, e.g., a truncated cylindrical recess with a major axis that lies along a lateral-medial line with respect to the endplate. In another embodiment not illustrated, the recess is a truncated spherical recess.

In one embodiment, one or both of endplates 38 and 40 of FIG. 3 are adapted to accommodate the core. For example, at least one of endplates 38 and 40 can define at least one recess to accommodate the core. In one embodiment, at least one of endplates 38 and 40 can define at least one recess to accommodate a plurality of core modules.

In some embodiments, the superior endplate of the intervertebral prosthetic disc includes an anterior plate (e.g., a first anterior plate) and a first posterior plate (e.g., a first posterior plate) and the anterior plate or the posterior plate defines a recess to accommodate the core. For example, the posterior plate can define a recess to accommodate the core. In some embodiments, the inferior endplate includes an anterior plate (e.g., a second anterior plate) and a posterior plate (e.g., a second posterior plate) and the anterior plate or the posterior plate defines a recess to accommodate the core. For example, the posterior plate can define a recess to accommodate the core. The core can include a plurality of core modules and, in those cases, the superior endplate or the inferior endplate can define a plurality of recesses to accommodate the plurality of core modules. However, in some embodiments, the superior endplate or the inferior endplate can define a single recess to accommodate a plurality of core modules.

The present invention includes an intervertebral prosthetic disc wherein the superior endplate defines a truncated spherical recess and the inferior endplate defines a plurality of truncated cylindrical recesses. The present invention also includes an intervertebral prosthetic disc wherein the inferior endplate defines a truncated spherical recess and the superior endplate defines a plurality of truncated cylindrical recesses.

The present invention is also directed to a method for installing a plate into an intervertebral space. A standard posterior or posterior-lateral surgical approach can be used. For example, the approach and exposure also used in a posterior lumbar interbody fusion (PLIF) operation or transforaminal lumbar interbody fusion (TLIF) operation can be utilized. The method can include distraction of the disc space and complete or partial discectomy. Techniques for approach, exposure of the intervertebral space, distraction, and discectomy are well known in the art.

The method of the invention includes threading a first plate onto a first guidewire, wherein the first plate is adapted to receive the first guidewire; inserting the first plate into the intervertebral space; tensioning the first guidewire; and seating the first plate onto a first vertebral bone endplate. In one embodiment, the plate is a superior or inferior endplate or an anterior or posterior plate component thereof, described supra. For example, the method can include threading an anterior plate onto a first guidewire, wherein the anterior plate is adapted to receive the first guidewire; inserting the first plate into the intervertebral space; tensioning the first guidewire; optionally, inserting a posterior plate into the intervertebral space and joining the anterior plate to a posterior plate; and seating the anterior plate onto a first vertebral bone endplate.

Figure 6:
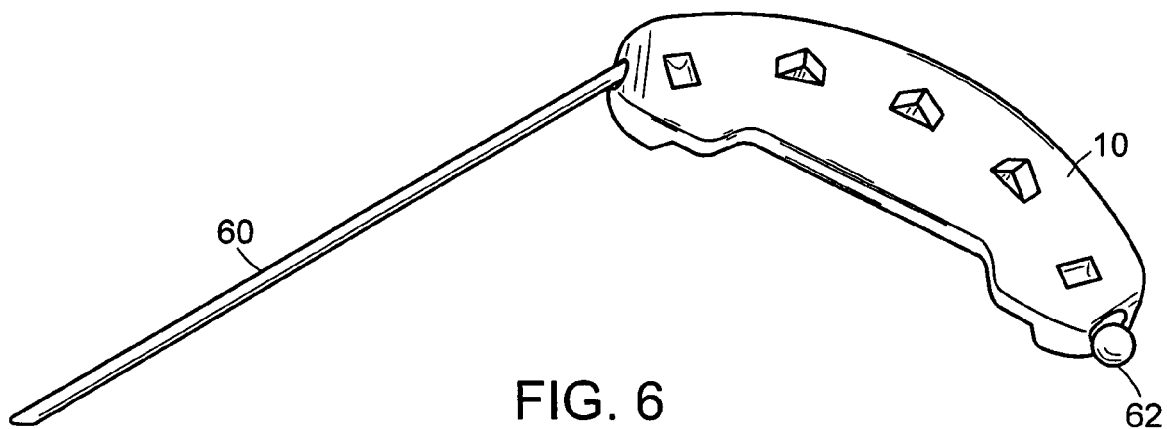
FIG. 6 is a perspective view of one embodiment of the present invention wherein an anterior plate of an endplate has been threaded onto a guidewire.

FIG. 6 illustrates a plate threaded onto a guidewire. As shown, anterior plate 10 has been threaded with guidewire 60. Guidewire stop 62 abuts anterior plate 10. The free end of the guidewire (i.e., the end opposite the guidewire stop) can be inserted into the anterior plate and pulled until the guidewire stop abuts the anterior plate.

Figure 7:
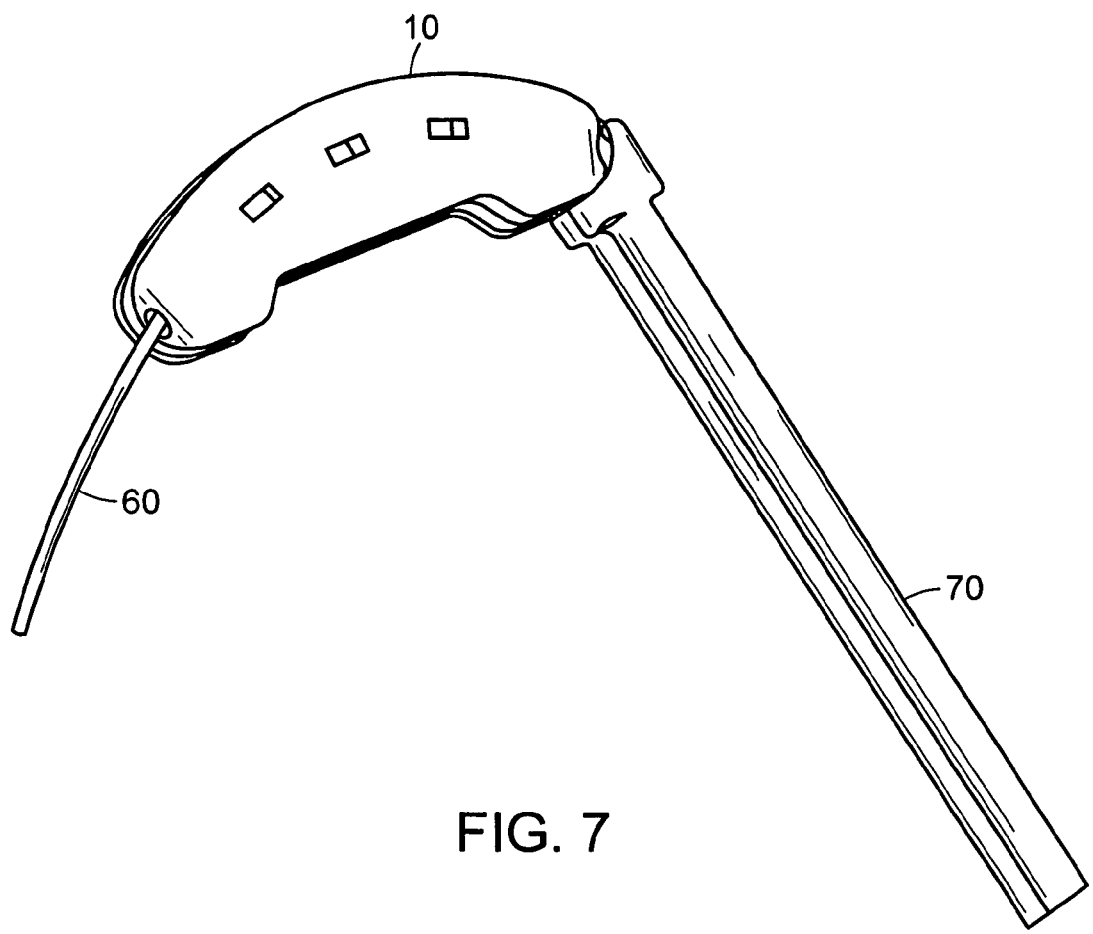
FIG. 7 is a perspective view of one embodiment of the present invention wherein an insertion device is used to hold an anterior plate of an endplate threaded onto a guidewire.

FIG. 7 shows an insertion device holding a plate threaded onto a guidewire. Insertion device 70 can grasp the plate, e.g., anterior plate 10, and prevent withdraw of guidewire 60 from the plate. For example, insertion device 70 can grasp anterior plate 10 at or near guidewire stop 62. In one embodiment, anterior plate 10 can contain a recess to receive a pinch tip on insertion device 70. In another embodiment, anterior plate 10 includes a threaded hole or a post to which insertion device 70 attaches. In one embodiment, insertion device 70 can be adapted to grasp guidewire stop 62. An insertion device, such as insertion device 70, can be used to insert the plate, e.g., anterior plate 10, into the intervertebral space. In one embodiment, an insertion device, such as insertion device 70, can be used to insert the plate, e.g., anterior plate 10, into the intervertebral space and to hold the plate during fixing of the plate to another plate, e.g., a posterior plate, to form an endplate.

Figure 8:
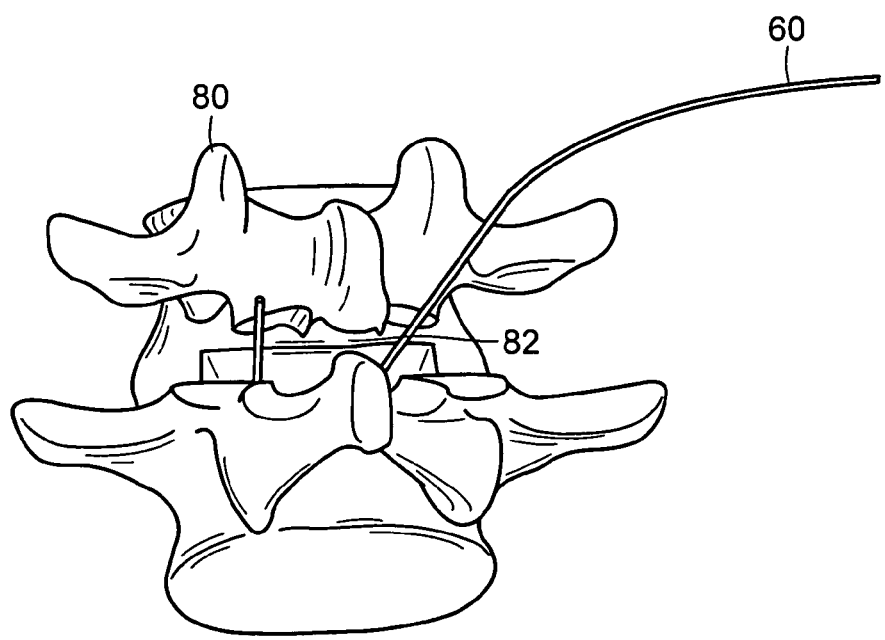
FIG. 8 is a partial view of a spinal column wherein an endplate threaded onto a guidewire has been inserted into an intervertebral space.

FIG. 8 is a partial view of spinal column 80 wherein an endplate threaded onto a guidewire 60 has been inserted into intervertebral space 82. In a preferred embodiment, the free end of the guidewire exits from intervertebral space 82 on the contra-lateral side.

In one embodiment, the method further includes threading a second plate onto a second guidewire, wherein the second plate is adapted to receive the second guidewire; inserting the second plate into the intervertebral space; tensioning the second guidewire; and seating the second plate onto a second vertebral bone endplate. In one embodiment, the second plate is a superior or inferior endplate or an anterior or posterior plate component thereof, described supra. For example, the method can include threading an anterior plate onto a second guidewire, wherein the anterior plate is adapted to receive the second guidewire; inserting the second plate into the intervertebral space; tensioning the second guidewire; optionally, inserting a posterior plate into the intervertebral space and joining the anterior plate to a posterior plate; and seating the anterior plate onto a second vertebral bone endplate.

Figure 9:
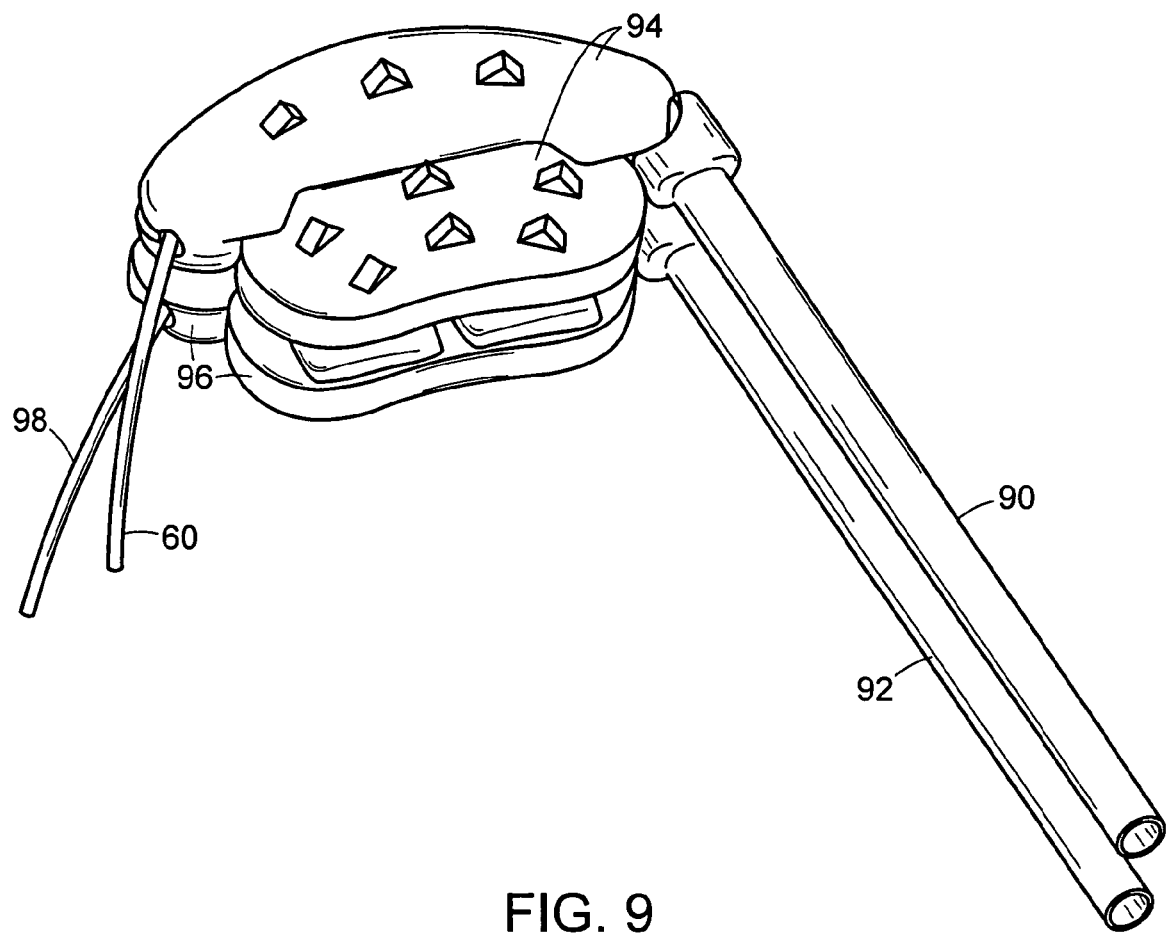
FIG. 9 is a view of an example superior endplate and an example inferior endplate held by insertion devices.

FIG. 9 shows endplates 90 and 92 threaded with guidewires 60 and 98 and held concurrently by two insertion devices 94 and 96. In one embodiment, the first and second plates are inserted into the intervertebral space concurrently. The endplates 90 and 92 can be aligned prior to concurrent insertion into the intervertebral space. Alternatively, endplates 90 and 92 can be inserted separately into the intervertebral space.

Advantageously, practice of the present invention allows a surgeon to install a plate into an intervertebral space using a posterior or a posterior-lateral approach. Therefore, in a preferred embodiment, one or both of the first and second plates are inserted into the intervertebral space using a posterior or a posterior-lateral approach.

The method also includes tensioning the guidewire. In one embodiment, tensioning the guidewire includes threading a cable tensioning device onto the guidewire and tensioning the guidewire using the cable tensioning device.

Figure 10A:
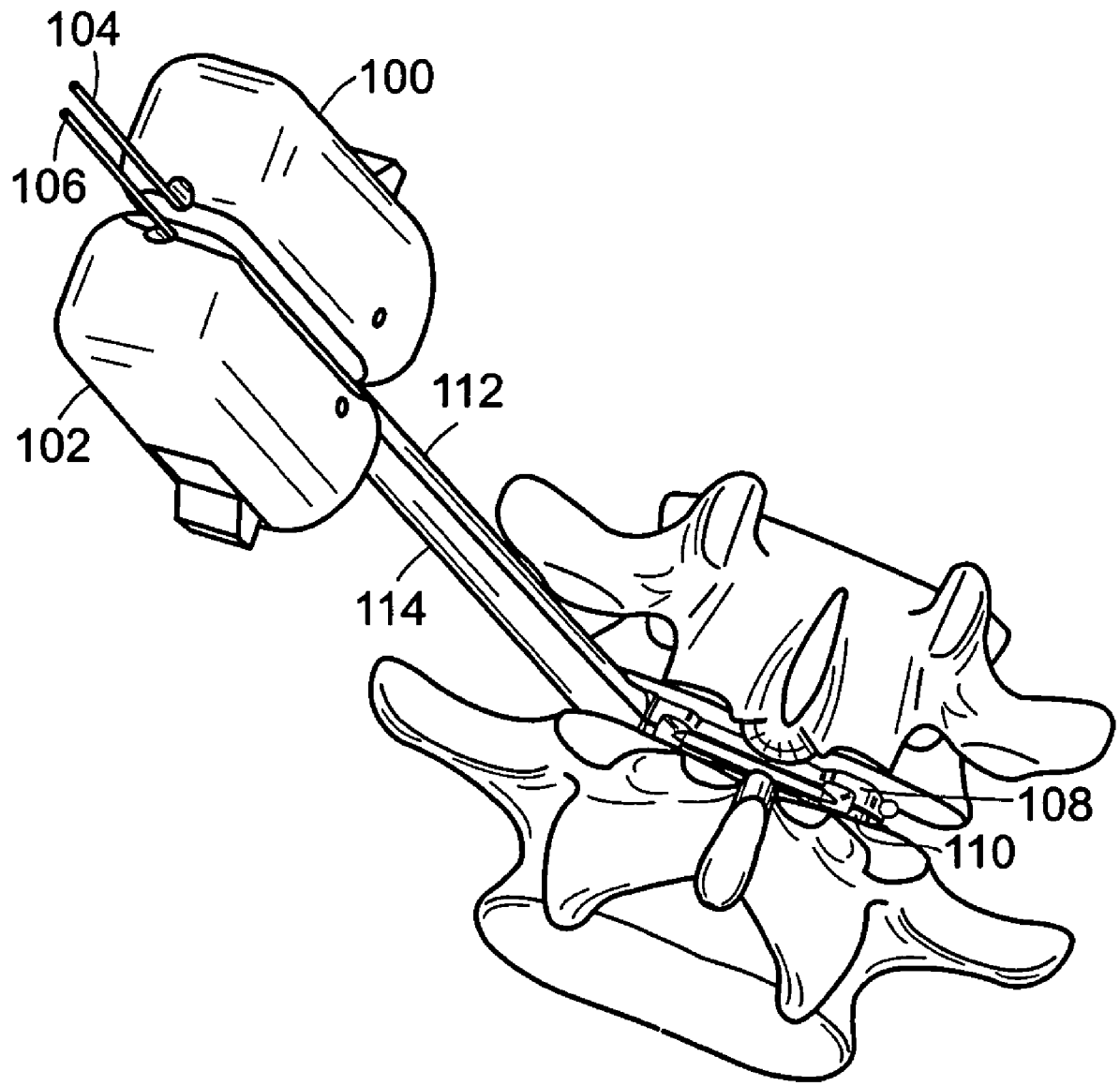
FIG. 10A is one view of two guidewires threaded onto cable tensioning devices after insertion of the guidewires and attached anterior plates into the intervertebral space.
Figure 10B:
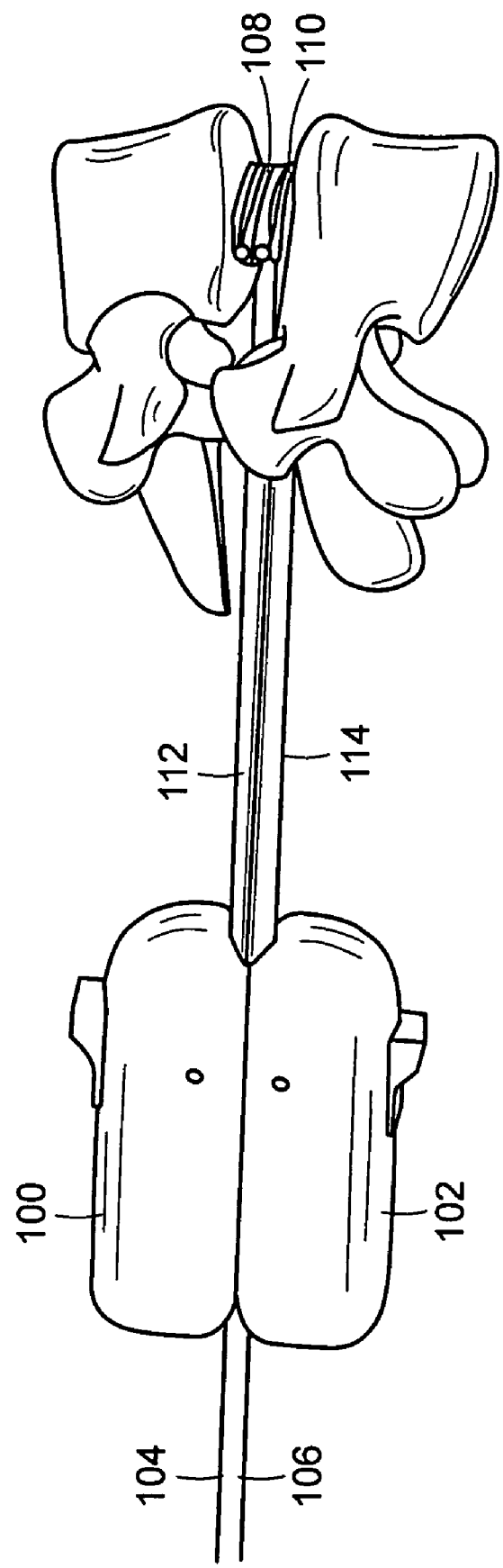
FIG. 10B is another perspective of the view of FIG. 10A.

FIGS. 10A and 10B illustrate a suitable cable tensioning device. Cable tensioning devices 100 and 102 are shown threaded over guidewires 104 and 106. Cable tensioning devices 100 and 102 pull guidewires 104 and 106 to impart tension in the guidewire connecting cable tensioning devices 100 and 102 and anterior plates 108 and 110. Cable tensioning devices 100 and 102 include instrument arms 112 and 114 and tensioning the guidewires can include rigidly positioning anterior plates 108 and 110 against instrument arms 112 and 114. In one embodiment, the instrument arm is adapted to align the plate with the arm in a predictable manner when tension is applied to the guidewire. For example, the end of the instrument arm can contain a cutout that aligns with an edge of the plate tensioned against the instrument arm, e.g., the geometry of the end of the instrument arm can match the geometry of an edge of the plate.

In one embodiment, the first plate is inserted into the intervertebral space prior to tensioning the first guidewire. In another embodiment, the first guidewire is tensioned prior to inserting the first plate into the intervertebral space. Likewise, in one embodiment, the second plate is inserted into the intervertebral space prior to tensioning the second guidewire. In another embodiment, the second guidewire is tensioned prior to inserting the second plate into the intervertebral space.

In one embodiment, the method further includes the step of joining a protrusion element to the first or second plates. As described supra, protrusion elements can be used to increase the surface area of an endplate that is presented to a vertebral bone endplate. In one embodiment, a protrusion element is joined to the first or second plates within the intervertebral space. By joining the protrusion element to the first or second plates within the intervertebral space, small elements can be introduced through the surgical incision, e.g., elements suitably sized for a posterior or posterior-lateral surgical approach, while a high surface area implantation can made to the vertebral bone endplate. In one embodiment, a plurality of protrusion elements are joined to the first and/or second plates. For example, the protrusion element can fit into a groove defined by the plate. In one embodiment, the groove defined by the plate contains a dovetail feature or interlocking feature for interaction with a corresponding structure on the protrusion element. A protrusion element can also contain a bulleted lead-in feature that facilitates joining the element to the plate.

The method for installing a plate into the intervertebral space also includes seating the plate onto a vertebral bone endplate, for example, seating the first plate onto a first vertebral bone endplate. Seating the plate onto a vertebral bone endplate can include positioning the plate within the intervertebral space. Methods for suitably positioning the plate can include aligning the instrument arm of the cable tensioning device, for example, using a template, thereby aligning the rigidly attached plate; positioning the plate using anatomical markers; and using computer assisted surgery (CAS) such as image guided surgery (IGS) or virtual fluoroscopy (VF).

Figure 11:
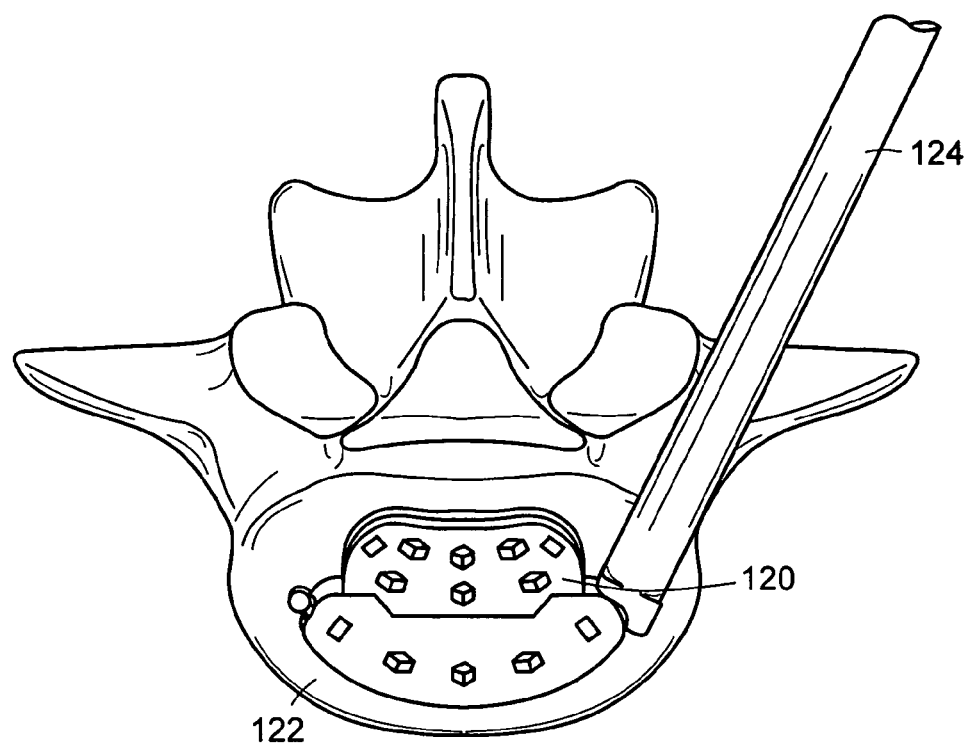
FIG. 11 is a view of assembled endplates of the intervertebral prosthetic disc positioned near the vertebral bone endplate.

FIG. 11 shows a view of assembled endplates 120 positioned near vertebral bone endplate 122 and rigidly attached to instrument arms 124. In one embodiment, an anterior plate and a posterior plate are joined together within the intervertebral space to form the assembled endplates 120.

Once suitably positioned in the intervertebral space, the plate can be finally seated onto a vertebral bone endplate. In one embodiment, the plate includes teeth and seating the plate onto the vertebral bone endplate includes pushing the teeth into the vertebral bone endplate. The plate can be seated into the vertebral bone endplate using any of several techniques known in the art. For example, a distraction instrument can be used to seat the plate onto the vertebral bone endplate.

Figure 12:
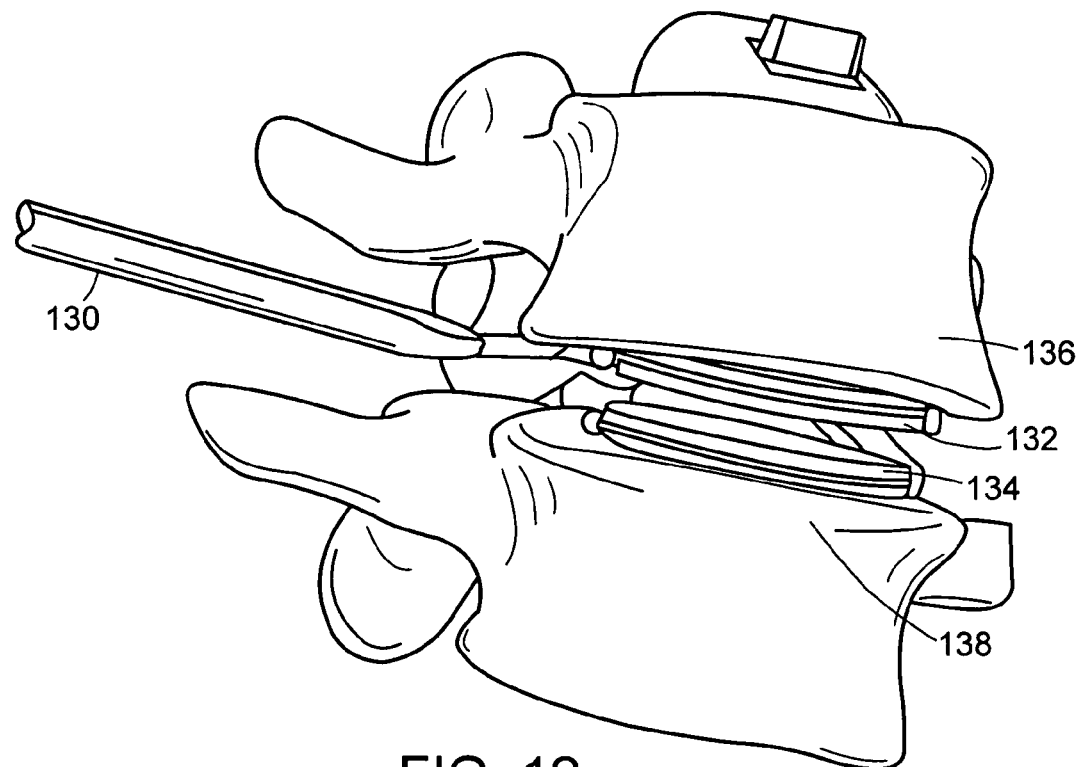
FIG. 12 illustrates use of a distraction device to seat the endplates.

FIG. 12 illustrates the use of distraction device 130 to seat endplates 132 and 134 into vertebral bone endplates 136 and 138.

The present invention also includes a method for installing a prosthetic disc into an intervertebral space. The prosthetic disc includes a first plate, an second plate, and a core. The method includes threading the first plate onto a first guidewire, wherein the first plate is adapted to receive the first guidewire; threading the second plate onto a second guidewire, wherein the second plate is adapted to receive the second guidewire; inserting the first plate and the second plate into the intervertebral space; tensioning the first and second guidewires; seating the first plate onto a superior vertebral bone endplate and seating the second plate onto an inferior vertebral bone endplate; and positioning the core between the first plate and the second plate.

Methods for threading the first plate onto a first guidewire; threading the second plate onto a second guidewire; inserting the first plate and the second plate into the intervertebral space; tensioning the first and second guidewires; and seating the first and second plates onto vertebral bone endplates are described supra. However, the method includes the additional step of positioning the core between the first plate and the second plate. The step of positioning the core can include placing the core into one or more recesses located on the inferior endplate. Positioning the core can also include using core trials to determine a suitably sized core. The spinal surgeon can select suitably sized cores based on techniques known to those of ordinary skill in the art. In one embodiment, a selection of core trials is provided to help determine the proper core size needed. Positioning the core can also include distracting the disc space as necessary. In one preferred embodiment, the core is positioned so that the core is accommodated by recesses in the superior endplate and in the inferior endplate. In one embodiment, the core is positioned into the disc space as core modules. For example, one core module is positioned in a recess of the inferior plate and then a second core module is positioned in a recess of the inferior plate. In one embodiment, the core modules are positioned so that the modules mate or abut.

Figure 13:
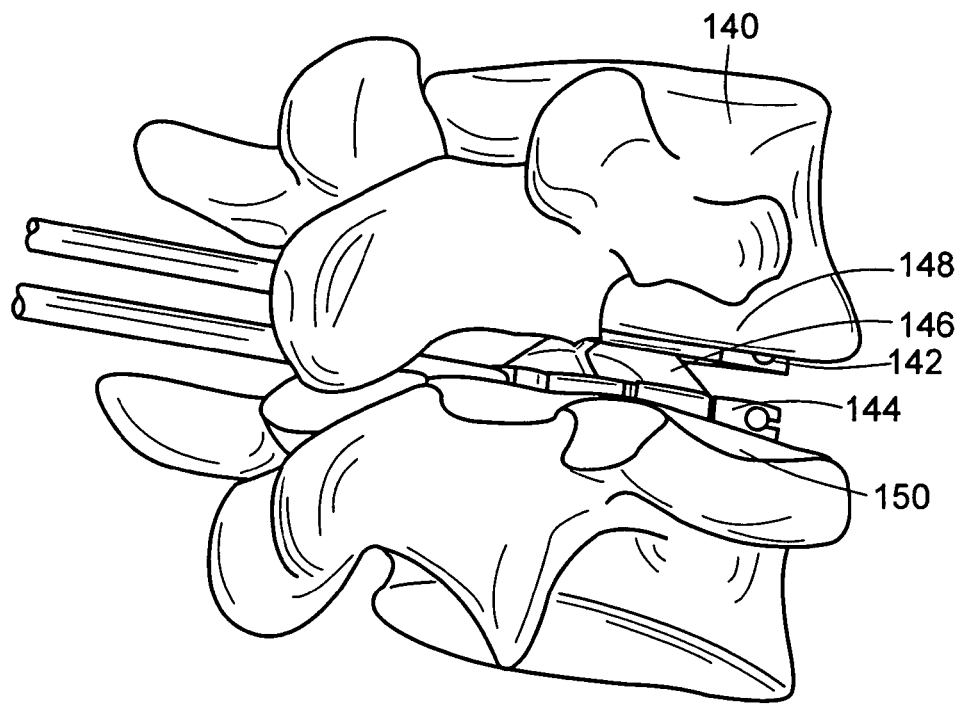
FIG. 13 illustrates a core positioned between assembled endplates seated into the vertebral bone endplates.
Figure 14:
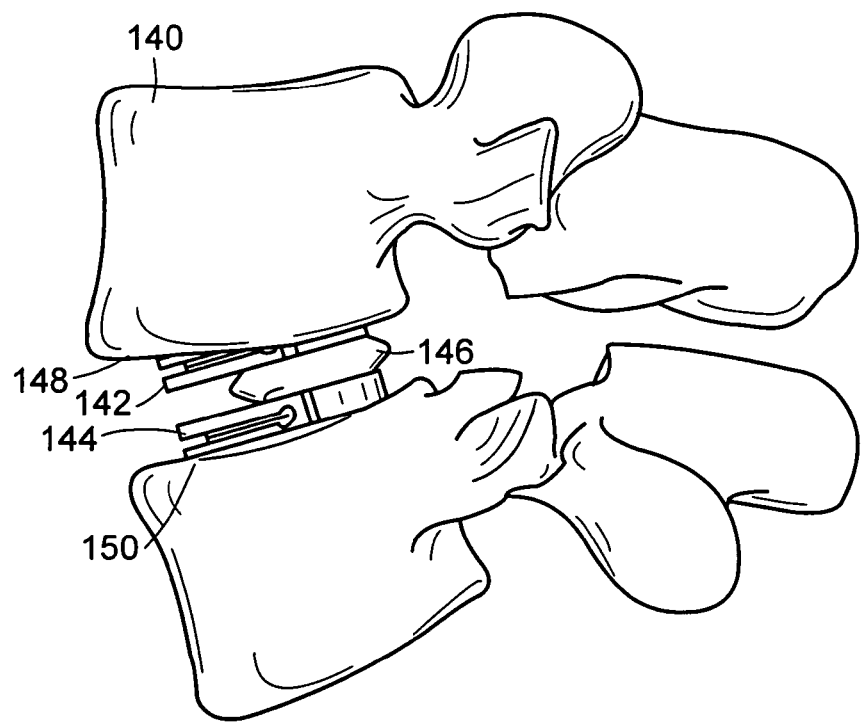
FIG. 14 illustrates a prosthetic disc, according to one embodiment, installed in the intervertebral space.

FIG. 13 illustrates, for example, core 146 positioned between assembled endplates 142 and 144 seated into vertebral bone endplates 148 and 150 of spinal column 140. FIG. 14 illustrates a prosthetic disc, according to one embodiment, installed in the intervertebral space. Core 146 is positioned between superior endplate 142, seated into vertebral bone endplate 148, and inferior endplate 144, seated into vertebral bone endplate 150.

Figure 15A:
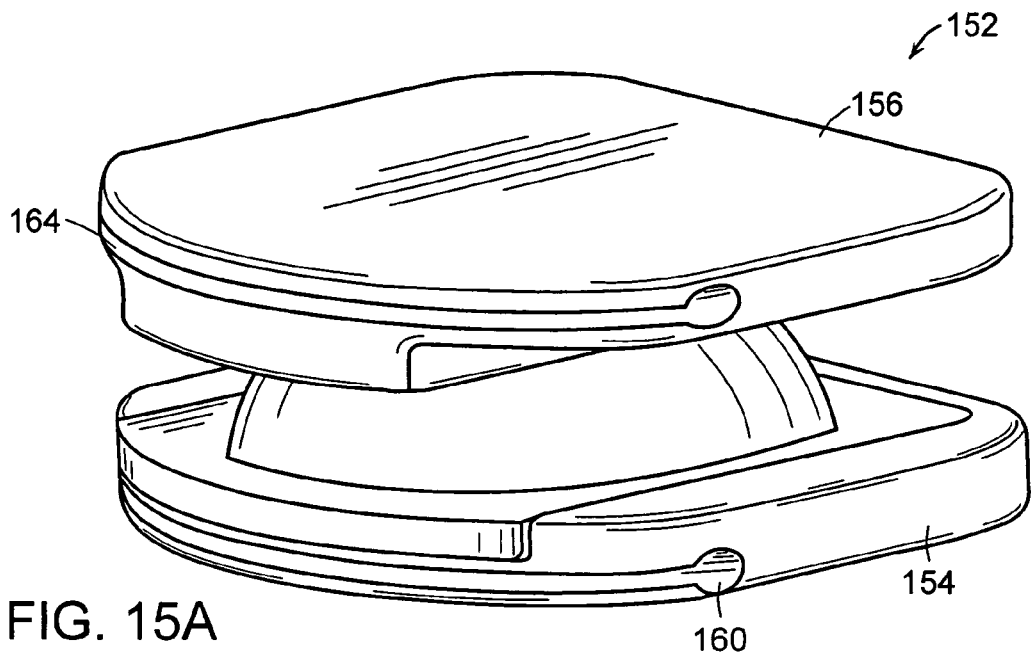
FIGS. 15A-15C illustrate an intervertebral prosthetic disc including a ball component and a socket component according to one embodiment of the present invention.
Figure 15B:
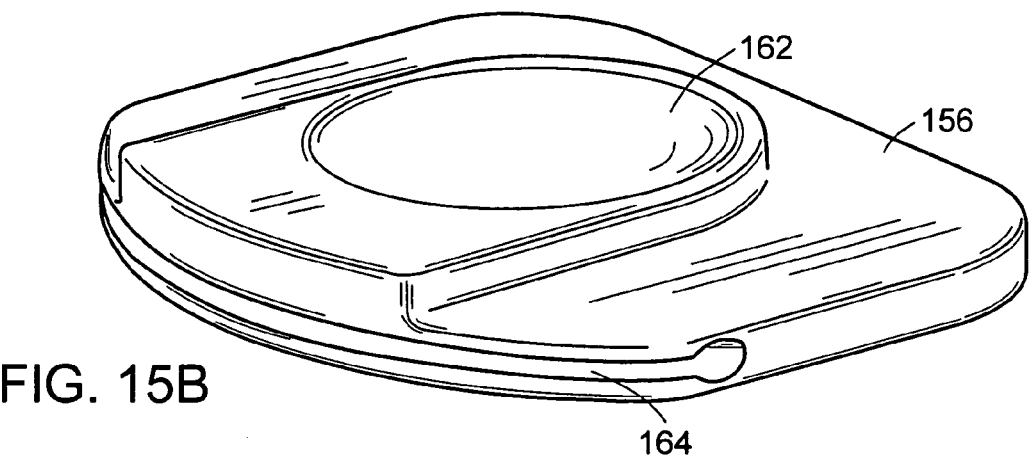
Figure 15C:
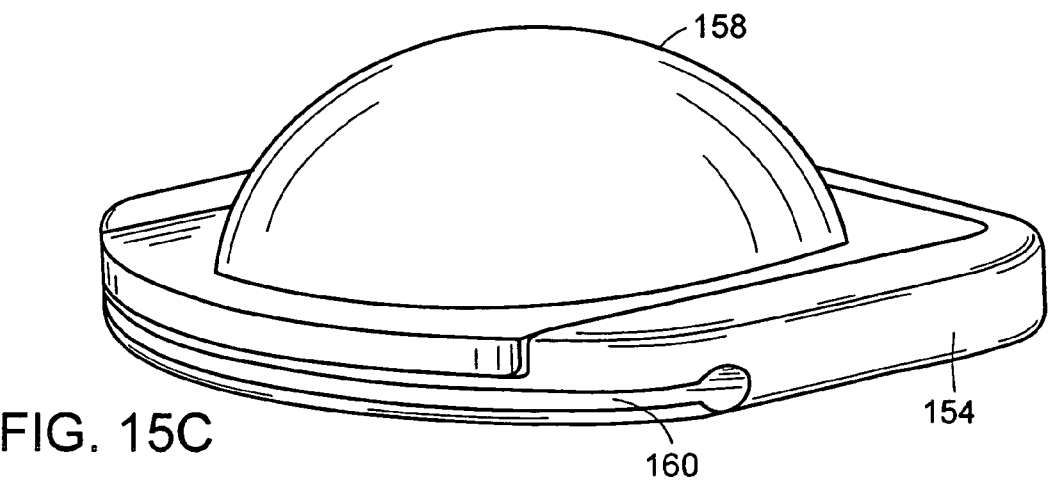

FIGS. 15A-15C illustrate intervertebral prosthetic disc 152 including a ball component and a socket component. Intervertebral prosthetic disc 152 includes endplates 154 and 156. Endplate 154 includes ball component 158 and guidewire channel 160. Endplate 156 includes socket component 162 for receiving ball component 158 and guidewire channel 164. In other embodiments, only one of endplates 154 and 156 includes a guidewire channel. In some embodiments, ball component 158 and socket component 162 are modular with endplates 154 and 156, respectively. For example, in one embodiment, ball component 158 is made of a different material than endplate 154 and ball component 158 mates with endplate 154. In other embodiments, ball component 158 and socket component 162 are integral with endplates 154 and 156, respectively. For example, in one embodiment, ball component 158 is made of the same material as endplate 154 and ball component 158 is integral with endplate 154.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. A method for installing a plate into an intervertebral space, comprising:
   threading a first plate onto a first guidewire, wherein the first plate is adapted to receive the first guidewire;
   inserting the first plate into the intervertebral space;
   tensioning the first guidewire;
   seating the first plate onto a first vertebral bone endplate;
   threading a second plate onto a second guidewire, wherein the second plate is adapted to receive the second guidewire;
   inserting the second plate into the intervertebral space;
   tensioning the second guidewire; and
   seating the second plate onto a second vertebral bone endplate.

2. The method of claim 1 wherein the first plate is inserted into the intervertebral space using a posterior or posterior-lateral approach.

3. The method of claim 1 wherein the second plate is inserted into the intervertebral space using a posterior or posterior-lateral approach.

4. The method of claim 1 wherein the first and second plates are inserted into the intervertebral space concurrently.

5. The method of claim 1 wherein the first and second plates are seated into the first and second vertebral bone endplates concurrently.

6. The method of claim 1 wherein tensioning the first guidewire includes threading a cable tensioning device onto the first guidewire and tensioning the first guidewire using the cable tensioning device.

7. The method of claim 6 wherein the cable tensioning device includes an instrument arm and tensioning the first guidewire includes rigidly positioning the first plate against the instrument arm.

8. The method of claim 1 wherein the first plate defines a guidewire channel with a generally lateral-medial orientation.

9. The method of claim 1 wherein the first plate includes a first anterior plate and a first posterior plate.

10. The method of claim 9 wherein threading the first plate onto the first guidewire includes threading the first anterior plate with the first guidewire, wherein the first anterior plate is adapted to receive the first guidewire.

11. The method of claim 9 wherein threading the first plate onto the first guidewire includes threading the first posterior plate with the first guidewire, wherein the first posterior plate is adapted to receive the first guidewire.

12. The method of claim 1 further comprising joining the first anterior plate and the first posterior plate within the intervertebral space, thereby forming the first plate.

13. The method of claim 1 further comprising joining a protrusion element to the first plate.

14. The method of claim 13 further comprising joining the protrusion element to the first plate within the intervertebral space.

15. The method of claim 1 further comprising joining a protrusion element to the second plate.

16. The method of claim 15 further comprising joining the protrusion element to the second plate within the intervertebral space.

17. A method for installing a prosthetic disc which includes a first plate, a second plate, and a core into an intervertebral space, comprising:
   a) threading the first plate onto a first guidewire, wherein the first plate is adapted to receive the first guidewire;
   b) threading the second plate onto a second guidewire, wherein the second plate is adapted to receive the second guidewire;
   c) inserting the first plate and the second plate into the intervertebral space;
   d) tensioning the first and second guidewires;
   e) seating the first plate onto a superior vertebral bone endplate and seating the second plate onto an inferior vertebral bone endplate; and
   f) positioning the core between the first plate and the second plate.

18. The method of claim 17 wherein the first and second plates are inserted into the intervertebral space using a posterior or posterior-lateral approach.

19. The method of claim 17 wherein the first and second plates are inserted into the intervertebral space concurrently.

20. The method of claim 17 wherein the first and second plates are seated into the first and second vertebral bone endplates concurrently.

21. The method of claim 17 wherein tensioning the first guidewire includes threading a cable tensioning device onto the first guidewire and tensioning the first guidewire using the cable tensioning device.

22. The method of claim 17 further comprising joining a protrusion element to at least one of the first plate and the second plate.

23. The method of claim 22 further comprising joining the protrusion element to at least one of the first plate and the second plate within the intervertebral space.

24. A method for installing a prosthetic disc which includes a first plate and a second plate into an intervertebral space, comprising:
   a) threading the first plate onto a first guidewire, wherein the first plate is adapted to receive the first guidewire;
   b) threading the second plate onto a second guidewire, wherein the second plate is adapted to receive the second guidewire;
   c) inserting the first plate and the second plate into the intervertebral space;
   d) tensioning the first and second guidewires; and
   e) positioning the first plate and the second plate within the intervertebral space.

25. The method of claim 24 further including seating the first plate onto a superior vertebral bone endplate and seating the second plate onto an inferior vertebral bone endplate.

26. The method of claim 24 further including positioning a core between the first plate and the second plate.

27. The method of claim 24 wherein the first plate includes a ball component and the second plate includes a socket component for receiving the ball component.

* * * * *